United States Patent
Vocks et al.

(10) Patent No.: US 12,145,808 B2
(45) Date of Patent: Nov. 19, 2024

(54) METHOD AND DEVICE FOR HANDLING (HYGIENE) PRODUCTS

(71) Applicant: Focke & Co. (GmbH & Co. KG), Verden (DE)

(72) Inventors: Matthias Vocks, Strücklingen (DE); Andreas Prahm, Barssel (DE); Arthur Wilhelm, Uplengen (DE); Torsten Kramer, Oldenberg (DE)

(73) Assignee: Focke & Co. (GmbH & Co. KG), Verden (DE)

( * ) Notice: Subject to any disclaimer, the term of this patent is extended or adjusted under 35 U.S.C. 154(b) by 129 days.

(21) Appl. No.: 18/003,408

(22) PCT Filed: Jun. 24, 2021

(86) PCT No.: PCT/EP2021/067300
§ 371 (c)(1),
(2) Date: Dec. 27, 2022

(87) PCT Pub. No.: WO2022/002743
PCT Pub. Date: Jan. 6, 2022

(65) Prior Publication Data
US 2023/0249921 A1   Aug. 10, 2023

(30) Foreign Application Priority Data

Jul. 1, 2020   (DE) .......................... 102020117315.6

(51) Int. Cl.
*B65G 47/32*    (2006.01)
*A61F 13/15*    (2006.01)
(Continued)

(52) U.S. Cl.
CPC ........ *B65G 47/32* (2013.01); *A61F 13/15764* (2013.01); *A61F 13/55105* (2013.01);
(Continued)

(58) Field of Classification Search
CPC ...... B65G 47/32; B65G 47/261; B65G 47/53; B65G 47/82; B65G 2201/02;
(Continued)

(56) References Cited

U.S. PATENT DOCUMENTS 4,768,642 A * 9/1988 Hunter ................. B65G 47/082
                                                                198/429
5,092,450 A * 3/1992 Schommartz .......... B65G 43/08
                                                                198/572
(Continued)

FOREIGN PATENT DOCUMENTS

CA   2849408 A1 * 9/2012 ........... B65B 25/146
CN   108438327 A * 8/2018 ............. B65B 19/34
(Continued)

OTHER PUBLICATIONS

Deutsches Patent- Und Markenamt (German Patent and Trademark Office), Recherchebericht (search in a related application), Mar. 29, 2021.

(Continued)

*Primary Examiner* — Gene O Crawford
*Assistant Examiner* — Muhammad Awais
(74) *Attorney, Agent, or Firm* — Laurence P. Colton; Smith Tempel Blaha LLC (57) ABSTRACT

A method and to a device for handling hygiene products, in particular nappies, wherein the products are transported by a feed conveyor in a first transport direction into compartments of a removal conveyor, in particular a grouping conveyor, which transports the products in a second transport direction, wherein the second transport direction extends transversely, in particular perpendicularly, to the first transport direction. At least one intermediate conveyor which serves to reduce the transport speed of the products in (Continued)

the first transport direction is located between the feed conveyor and the removal conveyor.

20 Claims, 5 Drawing Sheets

(51) Int. Cl.
    *A61F 13/551*     (2006.01)
    *B65G 47/26*     (2006.01)
    *B65G 47/53*     (2006.01)
    *B65G 47/82*     (2006.01)

(52) U.S. Cl.
    CPC ........... *B65G 47/261* (2013.01); *B65G 47/53* (2013.01); *B65G 47/82* (2013.01); *B65G 2201/02* (2013.01)

(58) Field of Classification Search
    CPC ............... B65G 47/841; B65G 47/082; A61F 13/15764; A61F 13/55105
    USPC ...................................... 198/459.1
    See application file for complete search history.

(56) References Cited

U.S. PATENT DOCUMENTS

| | | | | |
|---|---|---|---|---|
| 5,829,574 A * | 11/1998 | DelSanto | ............... | B65G 47/52 198/457.03 |
| 6,006,491 A * | 12/1999 | Mache | ............... | B65G 47/5109 53/154 |
| 7,475,525 B2 * | 1/2009 | Focke, legal representative | ........ | B65D 85/1072 53/158 |
| 8,056,304 B2 * | 11/2011 | Brandhorst | ............ | B65G 47/71 198/417 |
| 8,066,109 B2 * | 11/2011 | Engel | ..................... | B65H 29/40 198/419.3 |
| 2003/0057058 A1 * | 3/2003 | Iwasa | ................... | B65G 17/067 198/465.1 |
| 2003/0136086 A1 * | 7/2003 | Kalany | .................. | B65G 47/52 53/251 |
| 2007/0289842 A1 * | 12/2007 | Damhuis | ................ | B65G 47/32 198/434 |
| 2010/0138035 A1 * | 6/2010 | Fecht | ..................... | B65G 47/52 198/577 |

FOREIGN PATENT DOCUMENTS

| | | | | |
|---|---|---|---|---|
| DE | 3835058 A1 * | 4/1990 | | |
| DE | 102006005397 A1 * | 8/2007 | ........... | B65G 17/326 |
| DE | 102012208029 A1 * | 11/2013 | ............. | B65G 47/53 |
| EP | 0613838 A1 * | 9/1994 | | |
| EP | 0709315 A1 | 5/1996 | | |
| EP | 1052200 A1 * | 11/2000 | ........... | B65B 35/405 |
| WO | 2008135201 A2 | 11/2008 | | |

OTHER PUBLICATIONS

WIPO, International Searhc Report (in parent application), Sep. 10, 2021.

* cited by examiner

METHOD AND DEVICE FOR HANDLING (HYGIENE) PRODUCTS

CROSS REFERENCE TO RELATED APPLICATIONS

This application is the US national phase of and claims the benefit of and priority on International Application No. PCT/EP2021/067300 having an international filing date of 24 Jun. 2021, which claims priority on and the benefit of German Patent Application No. 10 2020 117 315.6 having a filing date of 1 Jul. 2020.

BACKGROUND OF THE INVENTION

Technical Field

The invention relates to a method for handling (hygiene) products, in particular diapers, the products being transported by way of a feed conveyor in a first transport direction into compartments of a discharge conveyor, in particular of a grouping conveyor, which transports the products in a second transport direction, the second transport direction running transversely, in particular perpendicularly, with respect to the first transport direction.

Furthermore, the invention relates to a corresponding apparatus for handling (hygiene) products, in particular diapers, with the feed conveyor for transporting the products in a first transport direction into compartments of a discharge conveyor, in particular of a grouping conveyor, the discharge conveyor being configured to transport the products in a second transport direction, and the second transport direction running transversely, in particular perpendicularly, with respect to the first transport direction.

Prior Art

During the production of collective packages for (hygiene) products, the procedure is often such that the products are fed to a compartment conveyor. The products are then fed in groups by the compartment conveyor to a corresponding packaging machine and are wrapped in a common cover. In the case of compartment conveyors which are known from practice, the products are introduced directly into the compartments. Here, the transport path of the products is braked by way of a stop, against which the products which are conveyed into the compartment conveyor bump.

One disadvantage of this procedure can consist in that the products which are conveyed into the compartment conveyor at a high speed bump against the stop, which can lead to an undesired deformation of the products.

BRIEF SUMMARY OF THE INVENTION

Proceeding herefrom, the invention is based on the object of developing methods and apparatuses of the type mentioned at the outset, in particular with regard to the elimination of the disadvantages of the prior art.

A method for achieving this object is a method for handling (hygiene) products, in particular diapers, the products being transported by way of a feed conveyor in a first transport direction into compartments of a discharge conveyor, in particular of a grouping conveyor, which transports the products in a second transport direction, the second transport direction running transversely, in particular perpendicularly, with respect to the first transport direction, characterized in that at least one intermediate conveyor which serves to decrease the transfer speed of the products in the first transport direction is arranged between the feed conveyor and the discharge conveyor. Accordingly, it is provided that at least one intermediate conveyor which serves to decrease the transfer speed of the products in the first transport direction is arranged between the feed conveyor and the discharge conveyor.

In this way, it is possible to avoid a deformation of the products by way of a stop, against which the products bump, or at least to decrease the risk of a deformation.

It can be provided in one preferred embodiment of the invention that the intermediate conveyor runs at least substantially parallel to the second transport direction.

The retardation can be achieved by virtue of the fact that the transport speed of the products in the first transport direction is decreased by way of temporary contact of the products with the intermediate conveyor or members thereof.

In other words, it can be provided that the transport speed of the products in the first transport direction is decreased by way of friction between the products and the intermediate conveyor or members thereof.

It is preferably provided that the intermediate conveyor and the discharge conveyor are driven continuously and at the same speed in the second transport direction, and that the two conveyors are configured as compartment conveyors and have dividing walls for dividing compartments of the respective conveyor, the two conveyors being driven in a manner which is oriented with respect to one another in such a way that the respective compartments and dividing walls are arranged so as to be aligned at least partially, with the result that the products are transported one after another by way of the feed conveyor through a compartment of the intermediate conveyor into a compartment of the discharge conveyor, the products being braked with regard to their transport speed in the first transport direction by way of partial contact or friction with the dividing walls of the intermediate conveyor and of the discharge conveyor.

A further special feature can consist in that regions of the products which protrude out of the compartments are stabilized by way of at least one further compartment conveyor, in particular by way of contact of the products with dividing walls of the further compartment conveyor, the or each further compartment conveyor being driven continuously in the second transport direction and preferably being arranged above the intermediate conveyor and/or the discharge conveyor.

In a configuration of this type, it can preferably also be provided that the compartment conveyor or the further compartment conveyors run obliquely with respect to the transport plane of the intermediate conveyor and/or discharge conveyor, with the result that the dividing walls of the compartment conveyor or the further compartment conveyors are withdrawn gradually from the products during the transport of the products in the second transport direction.

A further special feature can consist in that a diverter is arranged between the intermediate conveyor and the discharge conveyor, by way of which diverter the products are preferably pushed completely onto the discharge conveyor and/or are aligned on the discharge conveyor during the transport in the second transport direction.

An apparatus for achieving the object mentioned at the outset is an apparatus for handling (hygiene) products, in particular diapers, with the feed conveyor for transporting the products in a first transport direction into compartments of a discharge conveyor, in particular of a grouping conveyor, the discharge conveyor being configured to transport the products in a second transport direction, and the second transport direction running transversely, in particular perpendicularly, with respect to the first transport direction, characterized in that at least one intermediate conveyor is arranged between the feed conveyor and the discharge conveyor, for decreasing the transport speed of the products in the first transport direction. Accordingly, it is correspondingly provided that at least one intermediate conveyor is arranged between the feed conveyor and the discharge conveyor, for decreasing the transport speed of the products in the first transport direction.

It is preferably provided that the apparatus is configured to drive the intermediate conveyor and the discharge conveyor continuously and at the same speed in the second transport direction, and that the two conveyors are configured as compartment conveyors and have dividing walls for dividing compartments of the respective conveyor, the apparatus being configured to drive the two conveyors in a manner which is aligned with respect to one another in such a way that the respective compartments and dividing walls are arranged so as to be aligned at least partially, with the result that products are transported one after another by way of the feed conveyor through a compartment of the intermediate conveyor into a compartment of the discharge conveyor, the products being braked with regard to their transport speed in the first transport direction by way of partial contact with the dividing walls of the intermediate conveyor and the discharge conveyor.

It can be provided in one preferred embodiment of the invention that the compartments are dimensioned in such a way that they are only slightly wider than the respective product, with the result that the product is supported transversely with respect to the first transport direction by way of the compartment or its dividing walls.

A further special feature can consist in that regions of the products which protrude out of the compartments are stabilized by way of at least one further compartment conveyor, in particular by way of contact of the products with dividing walls of the further compartment conveyor, the or each further compartment conveyor being driven continuously in the second transport direction and preferably being arranged above the intermediate conveyor and/or the discharge conveyor.

In a configuration of this type, it can be provided, furthermore, that the compartment conveyor or the further compartment conveyors run obliquely with respect to the transport plane of the intermediate conveyor and/or discharge conveyor, with the result that the dividing walls of the compartment conveyor or the further compartment conveyors are withdrawn gradually from the products during the transport of the products in the second transport direction, in particular before the products pass into a deflecting region of the further compartment conveyor.

It is preferably provided that a diverter is arranged between the intermediate conveyor and the discharge conveyor, for preferably complete pushing of the products onto the discharge conveyor during the transport in the second transport direction and/or for aligning the products on the discharge conveyor.

A further special feature can consist in that the intermediate conveyor is configured in the second transport direction with a shorter extent than the discharge conveyor, and preferably extends only in a transfer region for the products.

One preferred detail of the invention can consist in that a plurality of dividing walls are combined to form compartment segments with a plurality of dividing walls which are spaced apart from one another.

Furthermore, it can be provided that the compartment segments are connected via a quick release fastener system to the corresponding conveyor, in particular to a toothed belt of the respective conveyor.

It can be provided in one preferred embodiment of the invention that in each case one additional compartment conveyor which is driven in the second transport direction is arranged above the intermediate conveyor and above the discharge conveyor.

BRIEF DESCRIPTION OF THE DRAWINGS

One preferred exemplary embodiment of the invention will be described in the following text on the basis of drawings, in which.

DETAILED DESCRIPTION OF PREFERRED EMBODIMENTS

Figure 1:
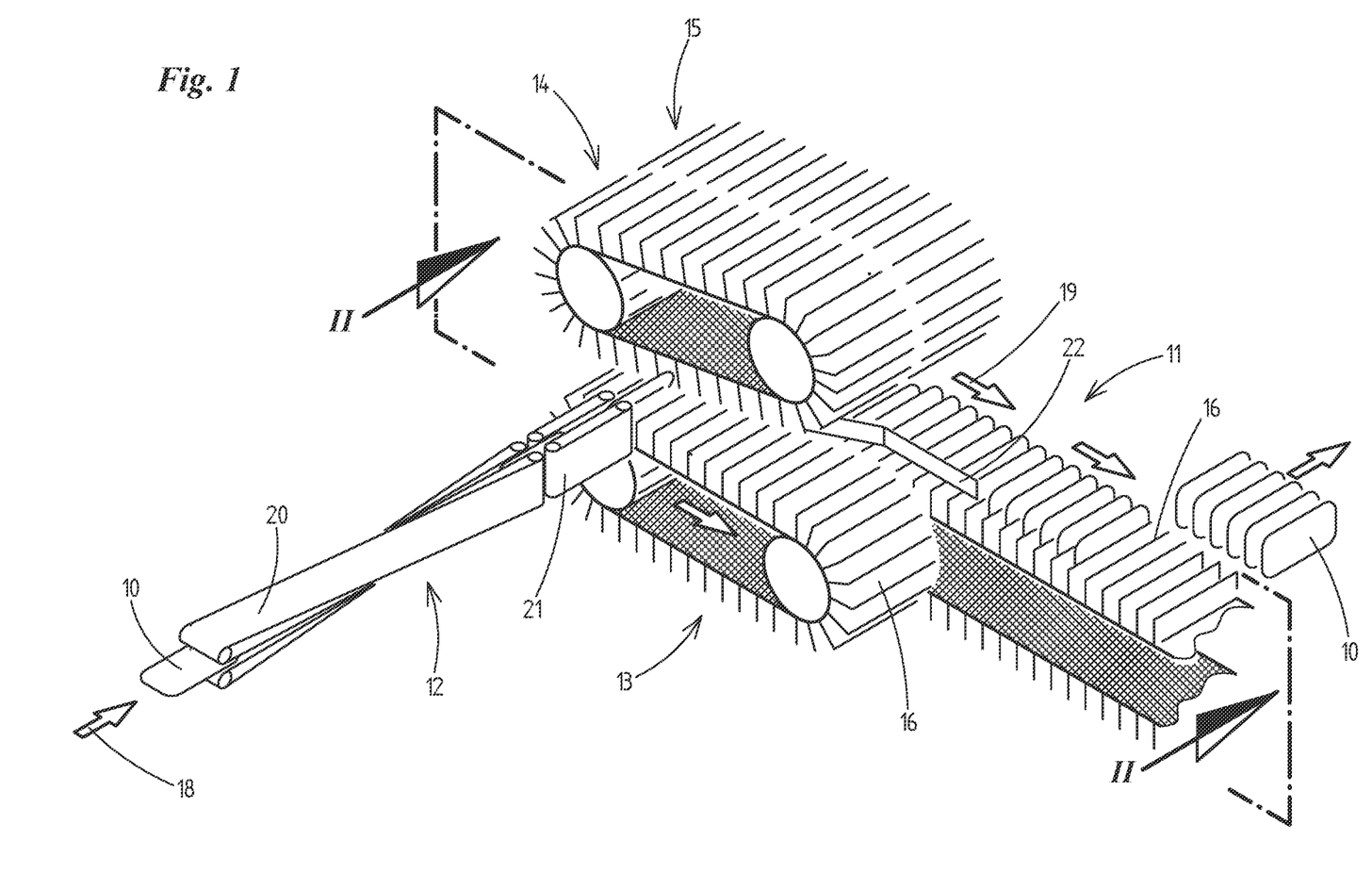
FIG. 1 shows an apparatus for handling (hygiene) products in a diagrammatic three-dimensional illustration.
Figure 2:
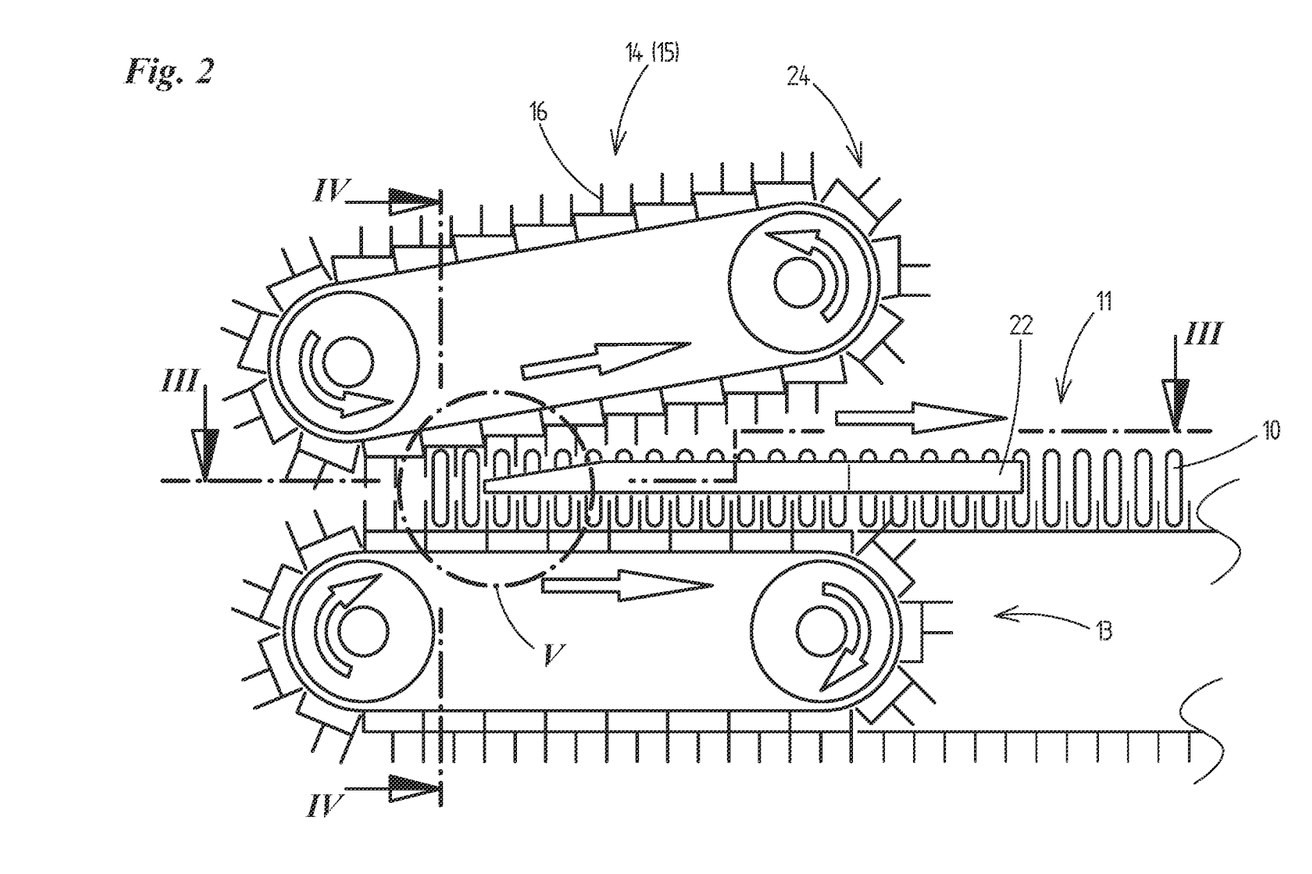
FIG. 2 shows a vertical section through the apparatus along the sectional line II-II in FIG. 1.
Figure 3:
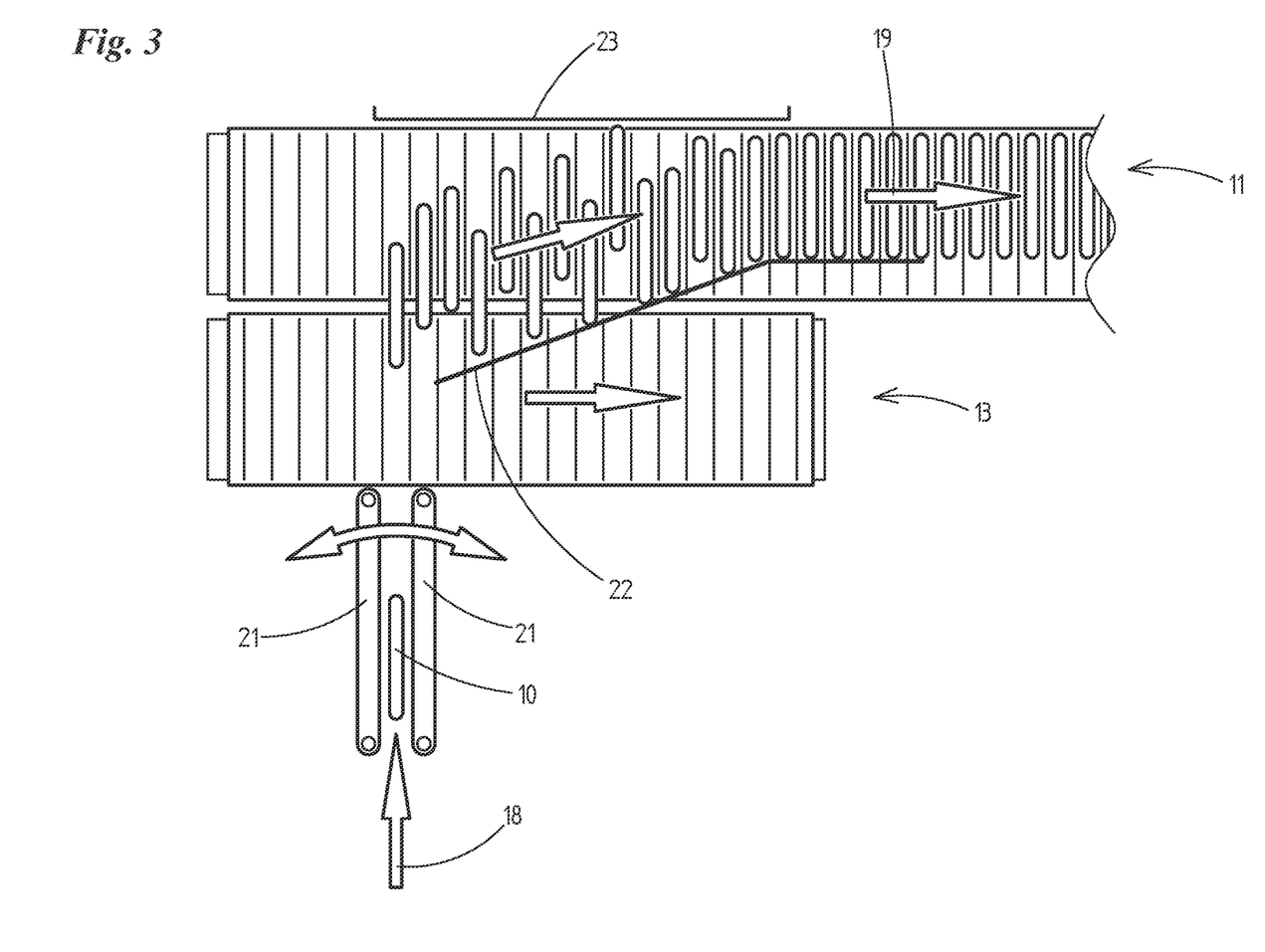
FIG. 3 shows a horizontal section through the apparatus along sectional line III-III in FIG. 2.
Figure 4:
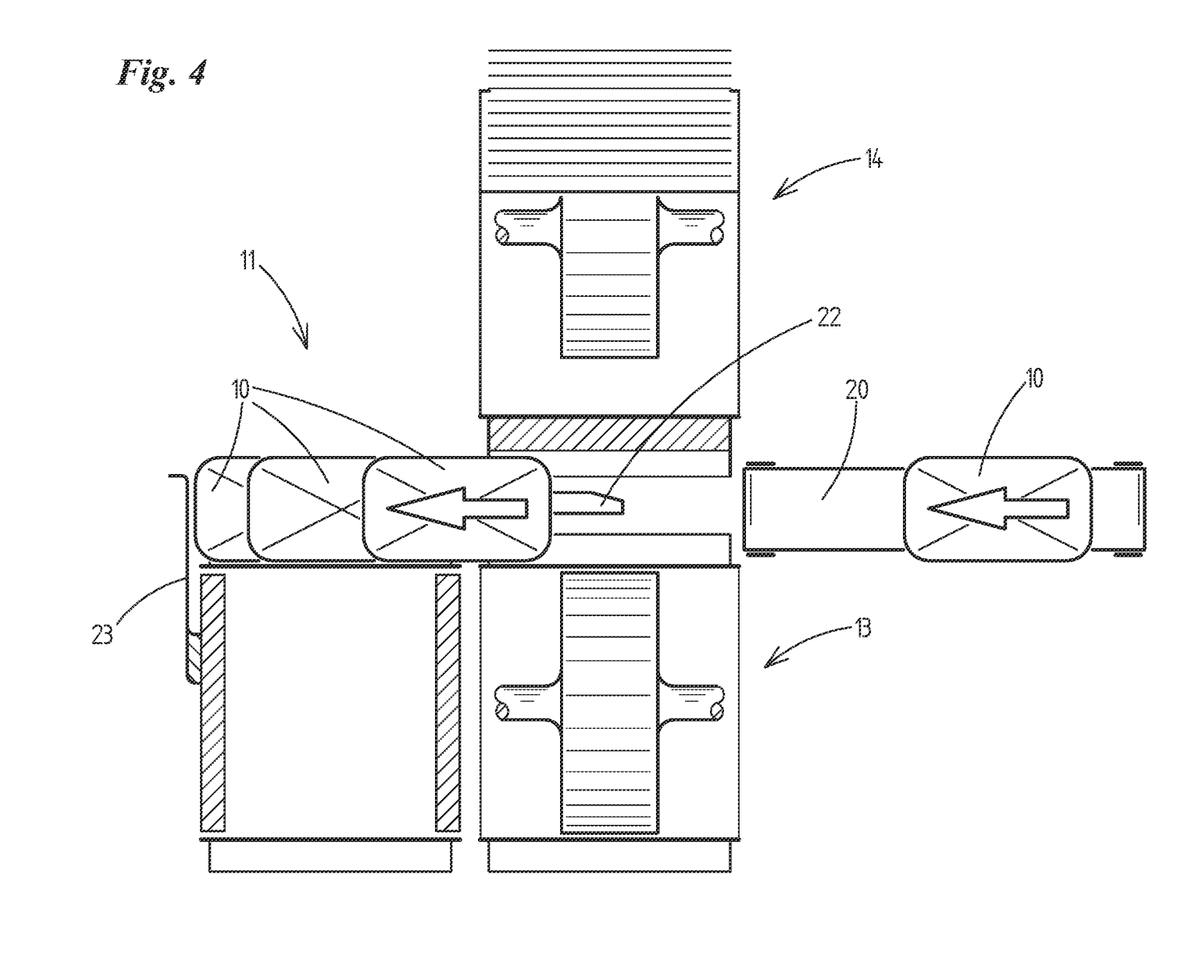
FIG. 4 shows a vertical section through the apparatus along sectional line IV-IV in FIG. 2.

The apparatus, essential parts of which are shown in FIG. 1, serves to handle diapers. It goes without saying that the apparatus is of course also suitable for handling similar hygiene products, with the result that products 10 will generally be addressed in the following text.

The products 10 are fed to a discharge conveyor 11. A feed conveyor 12 serves to this end. An intermediate conveyor 13 is arranged between the feed conveyor 12 and the discharge conveyor 11. Two further compartment conveyors 14, 15 are situated above the discharge conveyor 11 and the intermediate conveyor 13.

The drive of the conveyors takes place continuously throughout. The products 10 are also correspondingly moved continuously.

The intermediate conveyor 13, the discharge conveyor 11 and the two further conveyors 14, 15 are all configured as compartment conveyors, that is to say dividing walls 16 are arranged on the periphery of the preferably endless conveying run of the conveyors, which dividing walls 16 preferably stand perpendicularly with respect to the conveying run and serve to form compartments 17 of the conveyors, in which compartments a product 10, but possibly also a plurality of products 10, is/are received. It goes without saying that the conveyors do not necessarily have to be configured as compartment conveyors, but rather that the term also includes similar configurations, in the case of which compartments are formed which are suitable for receiving the products 10 tend to be conveyed.

The apparatus has substantially two transport directions. A first transport direction 18 is stipulated by way of the feed conveyor 12. The second transport direction 19 runs transversely, preferably substantially perpendicularly with respect thereto. The second transport direction 19 corresponds to the longitudinal extent of the intermediate conveyor 13, the discharge conveyor 11 and the two compartment conveyors 14, 15.

The feed conveyor 12 is configured in two parts and first of all has a pair of twist bands 20 and, adjoining this, a pair of feed belts 21. The products 10 are fed such that they lie flat to the twist bands 20, and are set up right during the transport by means of the twist bands 20. Afterward, the products 10 are transferred to the feed belts 21 which serve to feed the products 10 one after another to the discharge conveyor 11.

The feed of the products 10 from the feed belts 21 to the discharge conveyor 11 takes place through the intermediate conveyor 13 or its compartments 17. The discharge speed of the feed belts 21 is correspondingly selected in such a way that the products 10 are transmitted through the compartments 17 of the intermediate conveyor 13 into corresponding compartments 17 of the discharge conveyor 11. Here, the products 10 necessarily come into contact with the dividing walls 16 of the intermediate conveyor 13 and are braked by way of the friction which occurs.

Here, the width of the compartments 17 transversely with respect to the first transport direction 18 are selected in such a way that a suitable brake effect occurs. The dividing walls 16 of the discharge conveyor 11 can also be used to brake the products 10, with the result that the products 10 land correctly at the end in the compartments 17 of the discharge conveyor 11 or at any rate bump only at a small speed against the stop 23 which is arranged for safety reasons so as to adjoin the discharge conveyor 11, without appreciable deformation of the products 10 taking place.

Since the intermediate conveyor 13 and the discharge conveyor 11 are driven continuously during the transport of the products 10, it is provided that that end of the feed belts 21 which lies downstream can be pivoted laterally and runs together with the compartments of the intermediate conveyor 13. In this way, it is prevented that the products 10 bump against the dividing walls 16 of the intermediate conveyor 13.

The dividing walls 16 of the intermediate conveyor 13 and the discharge conveyor 11 are aligned with respect to one another, with the result that aligned compartments 17 are formed on the intermediate conveyor 13 and the discharge conveyor 11.

Furthermore, a diverter 22 is provided in the course of the discharge conveyor 11, which diverter 22 possibly pushes the products 10 onto the discharge conveyor 11 and/or aligns the products 10 situated there in a row.

At the end of the discharge conveyor 11, the products 10 are ejected in groups from the compartments 17 of the discharge conveyor 11 and are processed further.

A further special feature with regard to the arrangement and alignment of the further compartment conveyors 14, 15 consists in that, as viewed in a top view, the further compartment conveyors 14, 15 are situated in each case above the intermediate conveyor 13 and the discharge conveyor 11. Moreover, the further compartment conveyors 14, 15 are arranged in an inclined manner with respect to the transport plane of the intermediate conveyor 13 and the discharge conveyor 11.

The further compartment conveyors 14, 15 serve to support an upper edge of the products 10 standing in the compartments 17, and thus to prevent buckling of the products 10. Secondly, it has to be ensured that the region, in which the further compartment conveyors 14, 15 can serve for support, ends before the products 10 pass into the deflection region of the further compartment conveyors 14, 15. Otherwise, this would namely lead to the products 10 being buckled in the deflection region of the further compartment conveyors 14, 15 by way of the dividing walls 16 of the first and second compartment conveyor 14, 15. The further compartment conveyors 14, 15 are correspondingly inclined so as to rise slightly in the transport direction, with the result that the products 10 are no longer supported laterally by way of the dividing walls 16 of the further compartment conveyors 14, 15 before the deflection point of the two conveyors is reached.

Figure 5:
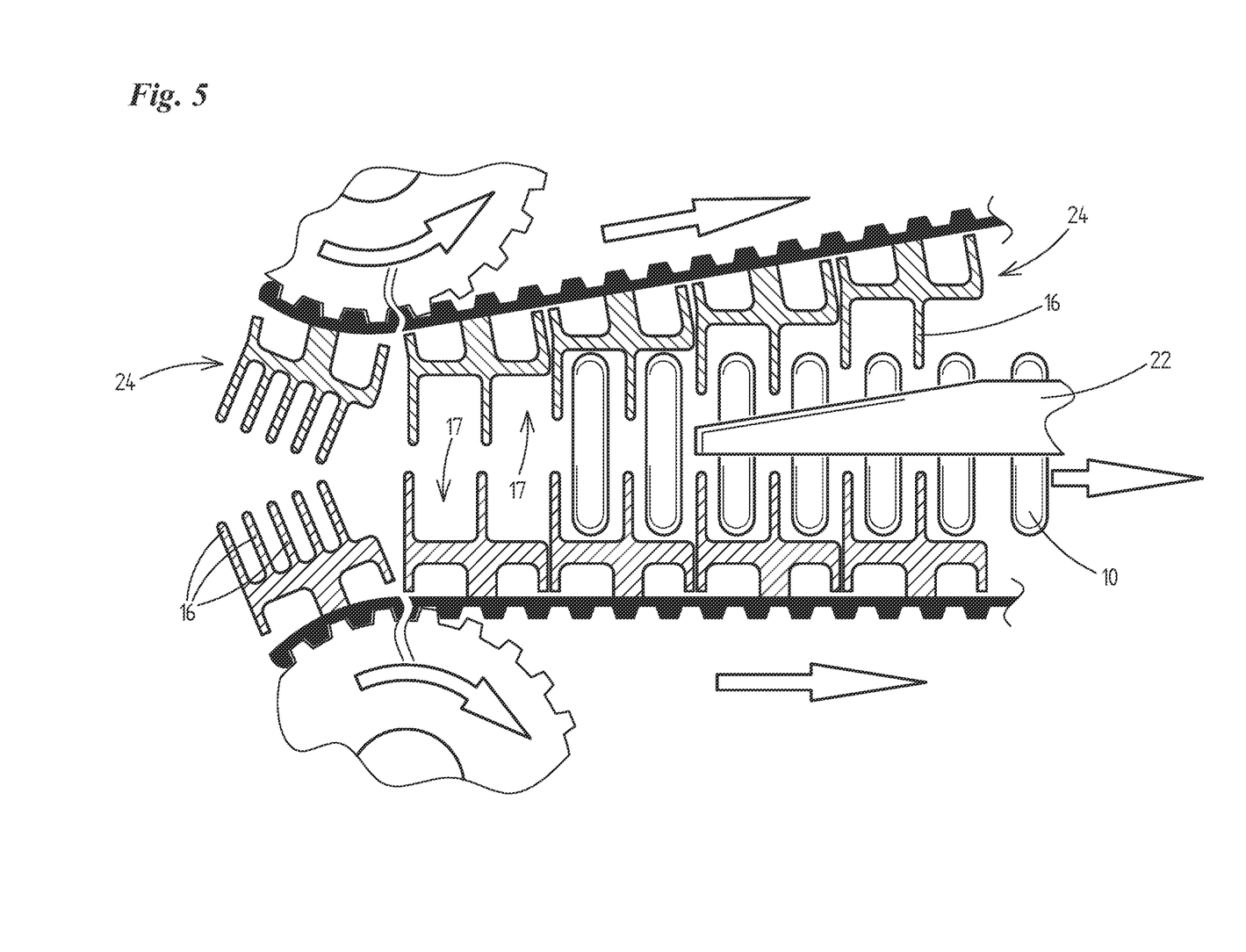
FIG. 5 shows a detail of the apparatus in the region V in FIG. 2.

As FIG. 5 shows, a plurality of dividing walls 16 are combined in each case to form a compartment segment 24. Compartment segments 24 with two dividing walls 16 and by way of example in each case one compartment segment with five dividing walls 16 are shown. The compartment segments 24 are connected via a quick release fastener system to the conveying run of the conveyors.

In summary, the method of operation of the apparatus can be described in other words, for instance, as follows:

The products 10 come such that they lie flat from a converter and are moved to a twisted conveyor belt 20. In the twisted conveyor belt 20, the products 10 are set perpendicularly and are conveyed at a high-speed to a stacker.

The stacker consists of four compartment belts 11, 13, 14, 15. The compartment segments 24 of the two compartment belts 11, 13 assume the lower guidance of the products 10, and the compartment segments 24 of the two compartment belts 14, 15 assume the upper guidance of the products 10.

After the products 10 have dipped into the compartments 17, they lose speed and come to a standstill in the region between the front compartment conveyors 13, 14 and rear compartment conveyors 11, 15. They have a particularly long run-out path and as a rule do not bump into the stop 23. As a result, the apparatus is particularly gentle to products. This means that the brake force is applied merely by way of the friction on the side surface of the product 10, and no deformation by way of the stop 23 takes place.

When the retardation operation of the products 10 is concluded, the upper compartment conveyors 14, 15 are pulled upward during the transverse movement. They serve only for two-sided guidance during the insertion, in order that no products 10 come to a standstill in compartment 17 which are not assigned to them.

In order that the compartment segments 24 of the front and rear compartment conveyor 14, 15 can pivot over at the deflection point, without bumping against the upper product edge, they have to be pulled out of the product region. This is brought about by way of oblique positioning of the compartment conveyors 14, 15.

Because the position of the products 10 in the compartments 17 is not defined when they come to a standstill, they are aligned by way of a diverter 22 during the transverse movement. After this equalization, they are fed by way of the discharge conveyor 11 to a bagger.

LIST OF DESIGNATIONS

10 Product
11 Discharge conveyor
12 Feed conveyor
13 Intermediate conveyor
14 Compartmentalized conveyor
15 Compartmentalized conveyor
16 Dividing wall
17 Compartment
18 First transport direction
19 Second transport direction
20 Twist band
21 Feed belt
22 Diverter
23 Stop
24 Compartment segment

What is claimed is:

1. A method for handling hygiene products (10), in particular diapers, the products (10) being transported by way of a feed conveyor (12) in a first transport direction (18) into compartments (17) of a discharge conveyor (11), in particular of a grouping conveyor, which transports the products (10) in a second transport direction (19), the second transport direction (19) running transversely, in particular perpendicularly, with respect to the first transport direction (18), wherein at least one intermediate conveyor (13) which serves to decrease the transfer speed of the products (10) in the first transport direction (18) is arranged between the feed conveyor (12) and the discharge conveyor (11), wherein the intermediate conveyor (13) and the discharge conveyor (11) are configured as compartment conveyors, wherein regions of the products (10) which protrude out of the compartments (17) are stabilized by way of at least one further compartment conveyor (14, 15), in particular by way of contact of the products (10) with dividing walls (16) of the further compartment conveyor (14, 15), wherein each further compartment conveyor (14, 15) being driven continuously in the second transport direction (19).

2. The method as claimed in claim 1, wherein the intermediate conveyor (13) runs at least substantially parallel to the second transport direction (19).

3. The method as claimed in claim 1, wherein the transport speed of the products (10) in the first transport direction (18) is decreased by way of temporary contact of the products (10) with the intermediate conveyor (13) or members thereof.

4. The method as claimed in claim 1, wherein the transport speed of the products (10) in the first transport direction (18) is decreased by way of friction between the products (10) and the intermediate conveyor (13) or members thereof.

5. The method as claimed in claim 1, wherein the intermediate conveyor (13) and the discharge conveyor (11) are driven continuously and at the same speed in the second transport direction (19), and in that the two conveyors are configured as compartment conveyors and have dividing walls (16) for dividing compartments (17) of the respective conveyor, the two conveyors being driven in a manner which is oriented with respect to one another in such a way that the respective compartments (17) and dividing walls (16) are arranged so as to be aligned at least partially, with the result that the products (10) are transported one after another by way of the feed conveyor (12) through a compartment (17) of the intermediate conveyor (13) into a compartment (17) of the discharge conveyor (11), the products (10) being braked with regard to their transport speed in the first transport direction (18) by way of partial contact or friction with the dividing walls (16) of the intermediate conveyor (13) and of the discharge conveyor (11).

6. The method as claimed in claim 1, wherein each further compartment conveyor (14, 15) are arranged above at least one of the intermediate conveyor (13) and the discharge conveyor (11).

7. The method as claimed in claim 1, wherein the compartment conveyor or the further compartment conveyors (14, 15) run obliquely with respect to the transport plane of at least one of the intermediate conveyor (13) and the discharge conveyor (11), with the result that the dividing walls (16) of the compartment conveyor or the further compartment conveyors (14, 15) are withdrawn gradually from the products (10) during the transport of the products (10) in the second transport direction (19).

8. The method as claimed in claim 1, further comprising a diverter (22) arranged between the intermediate conveyor (13) and the discharge conveyor (11).

9. An apparatus for handling hygiene products (10), in particular diapers, with the feed conveyor (12) for transporting the products (10) in a first transport direction (18) into compartments (17) of a discharge conveyor (11), in particular of a grouping conveyor, the discharge conveyor (11) being configured to transport the products (10) in a second transport direction (19), and the second transport direction (19) running transversely, in particular perpendicularly, with respect to the first transport direction (18), comprising at least one intermediate conveyor (13) arranged between the feed conveyor (12) and the discharge conveyor (11), for decreasing the transport speed of the products (10) in the first transport direction (18), wherein the intermediate conveyor (13) and the discharge conveyor (11) are configured as compartment conveyors, and wherein regions of the products (10) which protrude out of the compartments (17) are stabilized by way of at least one further compartment conveyor (14, 15), in particular by way of contact of the products (10) with dividing walls (16) of the further compartment conveyor (14, 15), wherein each further compartment conveyor (14, 15) being driven continuously in the second transport direction (19).

10. The apparatus as claimed in claim 9, wherein the apparatus is configured to drive the intermediate conveyor (13) and the discharge conveyor (11) continuously and at the same speed in the second transport direction (19), and in that the two conveyors are configured as compartment conveyors and have dividing walls (16) for dividing compartments (17) of the respective conveyor, the apparatus being configured to drive the two conveyors in a manner which is aligned with respect to one another in such a way that the respective compartments (17) and dividing walls (16) are arranged so as to be aligned at least partially, with the result that products (10) are transported one after another by way of the feed conveyor (12) through a compartment (17) of the intermediate conveyor (13) into a compartment (17) of the discharge conveyor (11), the products (10) being braked with regard to their transport speed in the first transport direction (18) by way of partial contact with the dividing walls (16) of the intermediate conveyor (13) and the discharge conveyor (11).

11. The apparatus as claimed in claim 9, wherein the compartments (17) are dimensioned in such a way that they are only slightly wider than the respective product (10), with the result that the product (10) is supported transversely with respect to the first transport direction (18) by way of the compartment (17) or its dividing walls (16).

12. The apparatus as claimed in claim 10, wherein each further compartment conveyor (14, 15) are arranged above at least one of the intermediate conveyor (13) and the discharge conveyor (11).

13. The apparatus as claimed in claim 9, wherein the compartment conveyor or the further compartment conveyors (14, 15) run obliquely with respect to the transport plane of at least one of the intermediate conveyor (13) and the discharge conveyor (11), with the result that the dividing walls (16) of the compartment conveyor or the further compartment conveyors (14, 15) are withdrawn gradually from the products (10) during the transport of the products (10) in the second transport direction (19).

14. The apparatus as claimed in claim 9, further comprising a diverter (24) arranged between the intermediate conveyor (13) and the discharge conveyor (11).

15. The apparatus as claimed in claim 9, wherein the intermediate conveyor (13) is configured in the second transport direction (19) with a shorter extent than the discharge conveyor (11).

16. The apparatus as claimed in claim 10, further comprising a plurality of dividing walls (16) combined to form compartment segments (24) with a plurality of dividing walls (16) which are spaced apart from one another.

17. The apparatus as claimed in claim 12, wherein in each case one additional compartment conveyor (14, 15) which is driven in the second transport direction (19) is arranged above the intermediate conveyor (13) and above the discharge conveyor (11).

18. The method as claimed in claim 8, wherein by way of the diverter (22) the products (10) are pushed completely onto the discharge conveyor (11) or are aligned on the discharge conveyor (11), or are pushed completely onto the discharge conveyor (11) and aligned on the discharge conveyor (11), during the transport in the second transport direction (19).

19. The apparatus as claimed in claim 14, wherein the diverter (24) is arranged for at least one of complete pushing of the products (10) onto the discharge conveyor (11) during the transport in the second transport direction (19) and aligning the products (10) on the discharge conveyor (11).

20. The apparatus as claimed in claim 15, wherein the intermediate conveyor (13) extends only in a transfer region for the products (10).

* * * * *